United States Patent
Persaud et al.

(10) Patent No.: US 6,190,858 B1
(45) Date of Patent: *Feb. 20, 2001

(54) DETECTION OF CONDITIONS BY ANALYSIS OF GASES OR VAPOURS

(75) Inventors: Krishna Chandra Persaud, Cheadle; Allan John Syms, Lach Dennis, both of (GB)

(73) Assignee: Osmetech plc (GB)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/331,749
(22) PCT Filed: Dec. 24, 1997
(86) PCT No.: PCT/GB97/03543
  § 371 Date: Aug. 23, 1999
  § 102(e) Date: Aug. 23, 1999
(87) PCT Pub. No.: WO98/29563
  PCT Pub. Date: Jul. 9, 1998

(30) Foreign Application Priority Data

Jan. 2, 1997 (GB) .................................. 9700012

(51) Int. Cl.[7] .............. C12Q 1/00; C12Q 1/70; G01N 33/53

(52) U.S. Cl. .................. 435/4; 435/5; 435/7.2; 435/7.21; 435/7.22; 435/7.31; 435/7.32; 435/29; 435/30; 435/34; 435/283.1; 435/286.6; 435/286.5; 435/287.1; 435/287.5

(58) Field of Search .................. 435/4, 5, 7.2, 7.21, 435/7.22, 7.31, 7.32, 29, 30, 34, 283.1, 286.6, 286.5, 287.1, 287.5

(56) References Cited

FOREIGN PATENT DOCUMENTS

| | | |
|---|---|---|
| 0158497 | 10/1985 | (EP) . |
| WO 94 04705 | 3/1994 | (WO) . |
| WO 95 33848 | 12/1995 | (WO) . |
| 99/09407 A1 * | 2/1999 | (WO) . |

OTHER PUBLICATIONS

Parry et al, "Leg Ulcer Odour Detection Identifies Beta–Haemolytic Streptococcal Infection", Journal of Wound Care Oct., vol. 4, No. 9, 1995.

English translation of Berdagué et al, Viandes Prod. Carnés 14 (5) (1993) 135 Sep.–Oct.

S–W Ho, Chinese J. Microbiol Immunol. 19, (1986) 18 "Head–Space Gas–Liquid Chromatographic Analysis for Presumptive Identification of Bacteria in Blood Cultures".

Shiyouzou, Patent Abstracts of Japan JP 60130398 (Nov. 7, 1985).

(List continued on next page.)

*Primary Examiner*—Louise N. Leary
(74) *Attorney, Agent, or Firm*—Renner, Otto, Boisselle & Sklar, LLP (57) ABSTRACT

The invention discloses a method for monitoring at least one condition in a patient comprising the steps of (a) obtaining samples from the patient over a period of time; (b) flowing the samples, or gases associated with or produced by the samples, over at least one gas sensor; c) measuring the response or responses of the at least one gas sensor; and (d) correlating the response or responses with the occurrence or state of the at least one condition. A method for identifying a micro-organism comprising the steps of (a) providing at least one gas sensor; (b) compiling a database of responses to at least one known micro-organism under a variety of culturing conditions; c) abstracting gas or vapor from a detection region and flowing the same over the at least one gas sensor and observing the response of the sensor or sensors; and (d) comparing the response to the database.

38 Claims, 3 Drawing Sheets

OTHER PUBLICATIONS

Schneider et al, Digestion 32: 86–91 (1985) ($^{14}$C breath test for intestinal bacterial).

Gardner and Craven "Classification of bacteria age and type using an array of metal oxide sensors & pattern recognition techniques", $3^{rd}$ International Symposium on Olfaction and Electronic Noses, Nov. 3–6, 1996 (publication date not known).

Rosenberg (Ed) "Bad Breath: Research Perspectives" 1995.

Rossi et al "Rapid discrimination of meat products and bacterial strains using semiconductor gas sensors" Bioflavour Feb. 14–17, 1995.

Parry et al, "Detection of β–haemolytic streptococcal infection by analysis of leg ulcer odour", Proc. Annual Conference of Wound Management, (?Oct.) 1994, 135.

Gardner and Craven, Application of an Artificial Neural Network Based Electronic Nose to the Classification of Bacteria, EUFIT, 1994.

Greenfield, "AromaScan sniffs out medical applications", Clinica, May 23, 1994.

Schweizer–Berberich et al, Characterisation of food freshness with sensor arrays, Sensors and Actuators B 18–19 (1994) 282.

Independent, "No business like nose business", Feb. 14, 1994.

Berdagué et al, Viandes Prod. Carnés 14(5) (1993) 135 Sep.–Oct.

Winquist et al, "Performance of an electronic nose for quality estimation of ground meat", Meas. Sci. Technol. 4,(1993) 1493.

Cowan and Steel's Manual for the Identification of Medical Bacteria ($3^{rd}$ edition 1993.)

MIDI Technical Notes #101, 102 (Identification of Bacteria by Gas Chromatography of Cellular Fatty Acids) ("Tracking" a Strain Using the Microbial Identification System) May 1990.

Ray Clement (Ed) "Gas Chromatography Biochemical, Biomedical and Clinical Applications", 1990.

Patent Abstracts of Japan JP 07 323034 A (Hitachi Ltd.), Dec. 12, 1995.

* cited by examiner

DETECTION OF CONDITIONS BY ANALYSIS OF GASES OR VAPOURS

This invention relates to the detection of conditions, in particular to the detection of conditions in a patient and the detection of microorganisms by analysis of gases or vapors emitted therefrom.

It is known that many gaseous or volatile species can be detected and identified by so-called "electronic noses", which are usually devices comprising an array of individual gas sensing elements. For example, the present applicants produce such an instrument having up to thirty two gas sensing elements, each element having a different semiconducting polymer. The semiconducting polymers typically display broad and overlapping responses towards gaseous species. However, this is turned to advantage when an array of such polymers is employed. On exposure to a gas or volatile species, the resistances of the semiconducting organic polymer vary—but to different extents. Thus the pattern of resistance variation across the array of sensors is indicative of the species being detected. Further information concerning polymers and the techniques used to interrogate them may be found in International Publication No. WO 96/00384 and references therein.

International Publication No. WO 95/33848 describes a method for detecting bacteria via detection of the characteristic vapors emanating therefrom as a result of bacterial metabolism by an array of gas sensors, in particular an array of semiconducting organic polymers of the type described above. The technique is of potentially wide and significant use in the medical area. However, to date, methods and apparatus suitable for practical, day to day use in a clinical environment have not been available. Furthermore, it would be desirable to detect and monitor a whole range of clinical conditions, which might include bacterial infections, but which might also include other conditions, such as viral or fungal infection.

The present invention addresses these problems and concerns.

According to a first aspect of the invention there is provided a method for monitoring at least one condition in a patient comprising the steps of:

obtaining samples from the patient over a period of time;

flowing the samples, or gases and/or vapors associated with, or produced by the samples, over at least one gas sensor;

measuring the response or responses of the at least one gas sensor as a function of time; and correlating the response or responses with the occurrence or state of the at least one condition.

In this way, monitoring for the onset of a condition, or monitoring of the progression of a condition is possible, the data being obtained very rapidly, since laborious and time consuming culturing steps are not required.

The samples may comprise respiratory gases.

The samples may comprise swabbed samples obtained from the patient.

The samples may comprise blood.

The condition monitored may be a disease state, and the progression and/or regression of the disease state may be monitored.

The condition may be a bacterial infection.

The condition may be a viral, fungal or parasitic infection.

The response or responses may be correlated with the effectiveness of a course of treatment.

The response or responses may be correlated with the progress of a healing process.

The response or responses may be correlated with the occurrence or state of the condition or conditions by a trained neural network.

An array of gas sensors may be employed. The pattern of responses of the sensors in the array may be correlated with the occurrence of or state of at least one condition.

The samples may be obtained continuously from the patient. The samples, or gas and/or vapor associated with or produced by the samples, may be continuously flowed over the at least one gas sensor. In this way, on-line monitoring of conditions by reference to gases and vapors is possible.

The response or responses of the at least one gas sensor may be measured continuously.

Alternatively, a plurality of measurements may be made over a period of time.

The samples may comprise respiratory gases obtained from a ventilator.

The samples may comprise blood undergoing a dialysis treatment. Gases produced by a waste product containing solution may be measured by the at least one gas sensor. The removal of urea from the blood sample may be monitored by measuring ammonia evolved from the waste product containing solution.

According to a second aspect of the invention there is provided a method for identifying a micro-organism comprising the steps of:

providing at least one gas sensor;

compiling a database of responses to at least one known micro-organism under a variety of culturing conditions;

abstracting gas and/or vapor from a detection region and flowing the same over said the at least one gas sensor and observing the response of the sensor or sensors; and comparing the response to the database.

The database may comprise responses to at least one known bacterium.

The database may comprise responses to a plurality of different isolates of a single bacterial species.

The mirco-organism may comprise a virus, fungus or parasite.

The database may comprise responses to at least one known micro-organism cultured under a variety of nutrient conditions.

The database may comprise responses to at least one known micro-organism cultured at a variety of temperatures.

The database may comprise responses to at least one known micro-organism obtained at different stages in the life cycle of the micro-organism.

The method may further identify at least one condition in a patient in which gas and/or vapor produced by the patient, or by a sample obtained from the patient, is flowed over the at least one gas sensor. At least a portion of the database may be compiled from responses of at least one gas sensor to gas or vapor produced by a patient, or by a sample obtained from the patient.

The database may comprise responses to at least one known micro-organism obtained at different stages during the course of treatment.

An array of gas sensors may be employed.

The compilation of the database may comprise training a neural network. In other words, the trained neural network is regarded as a "database" for the present purposes, and the pattern recognition processes employed by such networks are similarly regarded as "comparing the response to the database".

The response of the sensors may be used to provide information about the detection region, such as the nutrient conditions, the nature of the substrate or the location of the detection region.

The gas sensor or sensors may comprise a gas sensitive material. An electrical property of the gas sensitive material may vary on exposure to gases and/or vapors.

The gas sensitive material may comprise semi-conducting polymer.

The gas sensor or sensors may comprise metal oxide semiconductor (MOS), quartz resonator or surface acoustic wave (SAW) devices.

Methods and apparatus in accordance with the invention will now be described with reference to the accompanying drawings, in which.

BRIEF DESCRIPTION OF DRAWINGS

The invention comprises, in one aspect, a method for monitoring at least one condition in a patient comprising the steps of:
  obtaining samples from the patient over a period of time;
  flowing the samples, or gases and/or vapors associated with or produced by the samples, over at least one gas sensor;
  measuring the response or responses of the at least one gas sensor; and
  correlating the response or responses with the occurrence or state of the at least one condition.

Although, as discussed above, it is known from International Patent Publication No. WO 95/33848 that bacteria can be identified by way of detecting characteristic gases, the application of this technique to a clinical environment has not been forthcoming. The present invention enables monitoring of a patient over a period of time via the detection of certain gases and vapors. The monitoring can be in order to detect the onset of a condition, or to monitor the progression of a condition. The condition can be a bacterial infection, but the monitoring of a wide range of other conditions is also within the scope of the invention. It should be noted that the patient can be human, but the technique might be applied to the monitoring of conditions in animals.

International Publication No. WO 95/33848 only describes results obtained from cultured samples or bacteria. It is a considerable advantage of the present invention that measurements can be performed more or less directly upon samples obtained from the patient, since data is obtained very rapidly, with no need for laborious and time consuming culturing steps to be performed. It is surprising that such measurements can be made successfully, since the samples are obtained from a complex environment of mixed flora and fauna. This makes it difficult to differentiate gases produced due to a given condition from gases produced by other conditions and processes. In techniques in which a separate culturing process is performed under defined nutrient conditions and temperatures, the production of certain micro-organisms over other micro-organisms which require different culturing conditions is favoured. Therefore, the use of a culturing process inevitably involves a pre-selection of the micro-organisms identifiable by any subsequent detection method. The present invention does not involve such a pre-selection, it being sufficiently sensitive to make measurements on samples directly obtained from the patient, without requiring the population enhancement occurring during culturing.

The samples can comprise respiratory gases, in which instance the patient might exhale into a tube which communicates with the gas sensor or sensors, or into a bag which is sealed, the headspace in the bag being subsequently flowed across the sensor(s). Alternatively, samples might comprise swabbed samples obtained from the patient. The swabs can be placed in a closed environment, so that a headspace is developed which contains gases and vapors produced from the swabbed samples. The headspace is then flowed across the sensor(s) in ways well known in the art. Alternatively still, the samples might comprise blood.

An important aspect of the invention is on-line monitoring of a patient. In this aspect, samples are obtained continuously from the patient. Usually, the samples, or gas and/or vapor associated with or produced by the samples, are continuously flowed over the gas sensor(s). The response(s) of the gas sensor(s) can be measured continuously—which represents a totally "on-line" system—or it may be desirable to make more occasional measurements, ie. a plurality of measurements may be made over a period of time.

Figure 5:
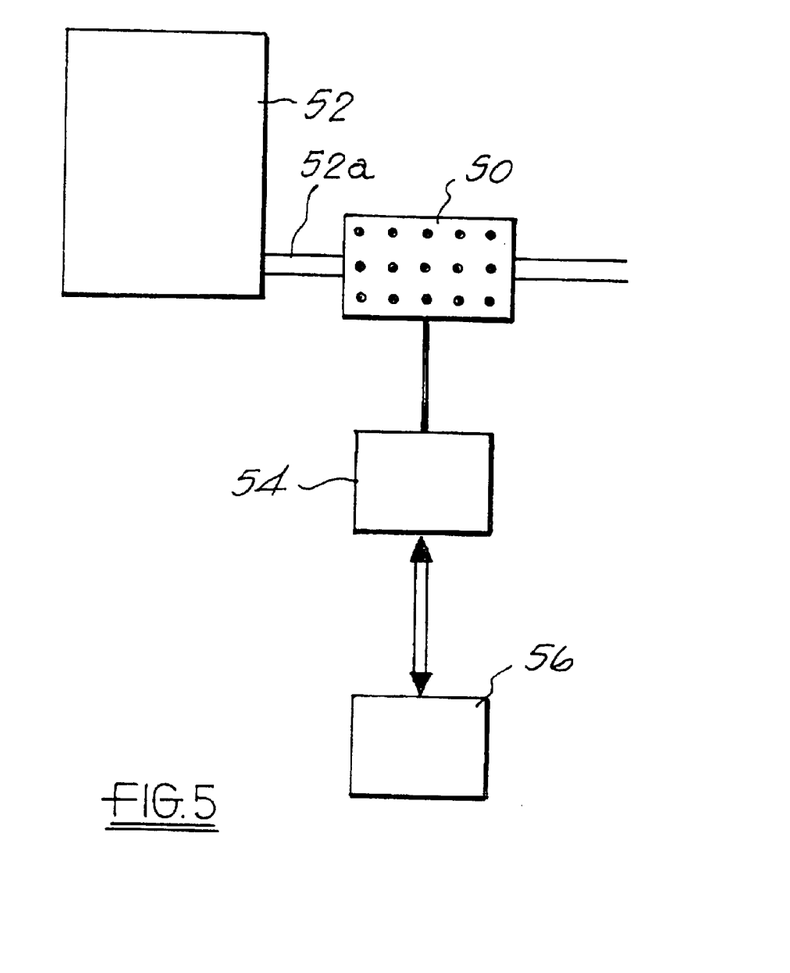
FIG. 5 is a schematic diagram of apparatus for on-line monitoring of respiratory gases.

FIG. 5 shows apparatus for on-line monitoring of at least one condition in a patient comprising:
  at least one gas sensor 50;
  sampling means 52 for continuously obtaining a sample from the patient and flowing the sample, or gases and/or vapors associated with or produced by the sample, over the at least one gas sensor 50; and
  measurement means 54 for measuring the response of the at least one gas sensor as a function of time.

In the embodiment shown in FIG. 5, the sample comprises respiratory gases and the sampling means 52 is a ventilator. The respiratory gases flow from the output 52a of the ventilator 52. In general, an array 50 of gas sensors is utilised although, as discussed more fully below, it is possible that a single gas sensor may suffice. The array 50 of gas sensors is positioned in direct communication with the output 52a of the ventilator, and thus continuously samples the respiratory gases of the patient. A computer 56 is employed to control the overall gas sensing procedure, and for data analysis purposes.

The gas sensors preferably comprise a gas sensitive material, ie. an active sensing medium, a property of which varies on exposure to the analyte gas. In preferred embodiments, an electrical property of the gas sensitive material varies on exposure to gases. The electrical property might be d.c. resistance, or an a.c. impedance property such as reactance or capacitance. It is also possible to monitor changes in optical or spectroscopic properties.

In a particularly preferred form of gas sensor, the gas sensitive material comprises semiconducting polymers. Examples of semiconducting polymers are polypyrrole and substituted derivatives thereof. Typically, gases are detected by measuring changes in the d.c. resistance of the polymer (see for example Persaud K C, Bartlett J G and Pelosi P, in "Robots and Biological Systems: Towards a new bionics?", Eds. Darios P, Sandini G and Aebisher P, NATO ASI Series F: Computer and Systems Sciences 102 (1993) 579). However, it is also possible to measure a.c. impedance properties, as taught by British Patent GB 2 203 553. Excellent results can be obtained if measurements of quantities related to the resonant frequency, such as dissipation factor, are performed, as taught by International Publication No. WO 97/19349. Alternative gas sensors include metal oxide semiconductor (MOS), quartz resonator or surface acoustic wave (SAW) devices. It is a feature of such gas sensors that they are not selective: an individual gas sensor is generally sensitive to a range of gases. One way of performing species selective identification is to employ an array of gas sensors having different response characteristics, and to observe the pattern of sensor responses across the array. The pattern of response represents a characteristic "fingerprint" for the measured gas. For the present purpose, an "array" should be considered as two or more gas sensors. In the case of semiconducting polymers in which measurements of d.c. resistances are made, the array typically comprises ten or more gas sensors, preferably twenty or more. However, the use of a.c. or like interrogation permits results in more information to be obtained from a single sensor, and thus fewer sensors are required in the array. It may be possible to employ a single gas sensor.

Using an array of gas sensors, the pattern of responses of the sensors in the array can be correlated with the occurrence of or state of the condition or conditions. The pattern of response can be transformed into 2 or 3 dimensional space by an appropriate transformation, such as a Salmon mapping algorithm. Such a transformation can be performed on the computer 56, and aids the identification of differences in patterns by humans. This is particularly important if the correlation of the response pattern with the condition(s) is performed by human judgement. Alternatively, or additionally, a neural network might be employed to assess the response pattern and perform the correlation.

It is a considerable advantage that the present invention may be applied to monitoring a wide range of conditions. The condition monitored can be a disease state. The purpose may be to detect the onset of such a condition, or to monitor the progression and/or regression of a disease state. The condition can be a bacterial, viral, fungal or parasitic infection. Furthermore, it is possible, as demonstrated in the Examples, to correlate the response(s) of the sensor(s) with the effectiveness of a course of treatment and/or the process of a healing process. The correlation of response(s) with the occurrence of certain condition or conditions might be performed by a skilled person, but advantageously it is performed by suitably adapted software, such as a trained neural network.

Returning to the on-line monitoring of conditions through gas detection, another important embodiment involves the on-line monitoring of dialysis. In the dialysis process, waste products diffuse across a membrane into a waste product containing solution and are thereby removed from the blood sample. Direct monitoring of gases and/or vapors associated with the blood is complicated by the fact that the blood is circulated in a closed system. Instead, it is preferable to detect gases and/or vapors produced by the waste product containing solution. In particular, the removal of urea from the blood sample may be monitored by measuring ammonia evolved from the waste product containing solution. Dialysis is complete when no further increases in ammonia concentration are detected.

EXAMPLE 1

The progress of chronic venous ulcers was monitored using a twenty sensor AromaScan A20S instrument in a confidential study.

Patients with chronic non-healing venous or mixed (venous and arterial) ulcers were studied. All had previously been treated by four-or three-layer bandaging over several weeks and had failed to improve. None had pure arterial disease (all Ankle Brachial Pressure Indices [ABPIs] were>0.6), diabetes mellitus, rheumatoid arthritis or other conditions associated with leg ulceration and poor wound healing. Each patient underwent a biopsy prior to the study.

The ulcers were dressed weekly with dressing maintained in contact with the ulcer surface by a four or three layer elastic bandage. The dressings were non-adherent contact dressings (Johnson and Johnson 'N/A'). Dressings were removed with forceps and placed into 250 ml Duran bottles. Before introduction to the A20S instrument, the Duran bottle cap was replaced with one having inlet and outlet ports (see FIG. 1). The Duran bottle was heated to 37° C. for 30 minutes and the headspace pumped across the sensor array. In this manner, weekly measurements of gases and vapors emanating from the contact dressings were made.

Eight men (mean age 69.6, range 52–81) and seven women (mean age 70.9, range 55–81) were entered into the study, which was conducted over a six month period. None of these fifteen ulcers appeared to be clinically infected.

Potentially pathogenic bacteria were cultured from thirteen out of the fifteen patients (see Table 1). Beta-haemolytic streptococci were cultured from the biopsies of eleven patients (often in mixed growth with other organisms). *Staphylococcus aureus* and *Peptostreptococcus sp.* were each isolated from a single patient. Patient underwent an appropriate course of treatment.

Figure 2:
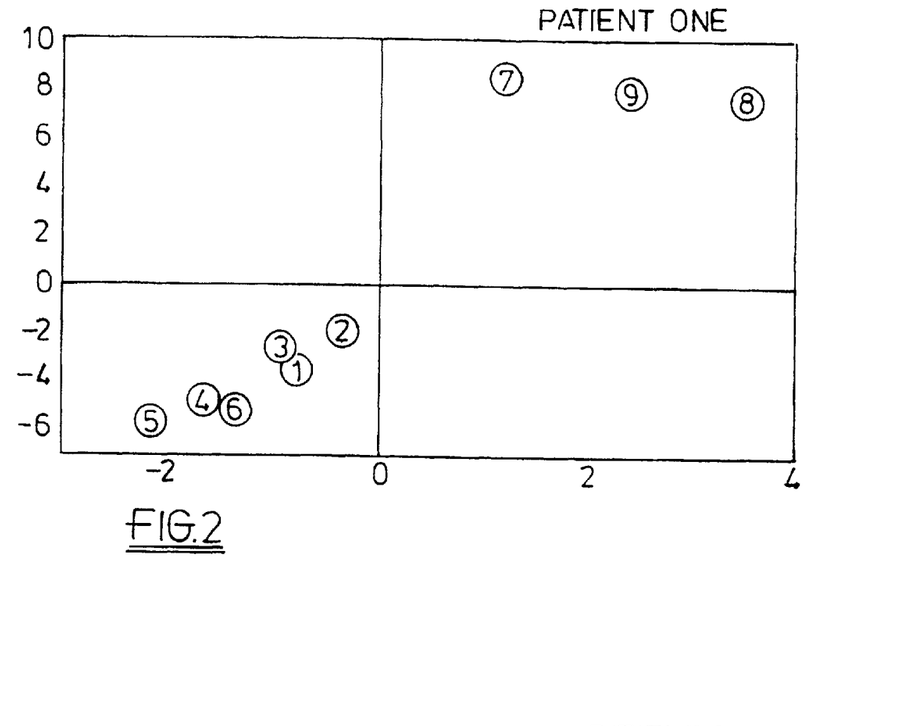
FIG. 2 shows response as a function of time for patient one.
Figure 3:
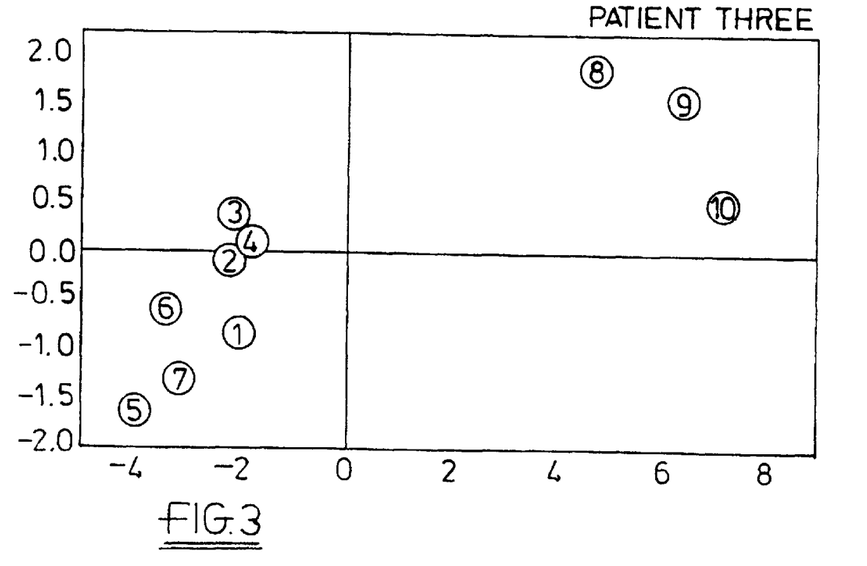
FIG. 3 shows response as a function of time for patient three.
Figure 4:
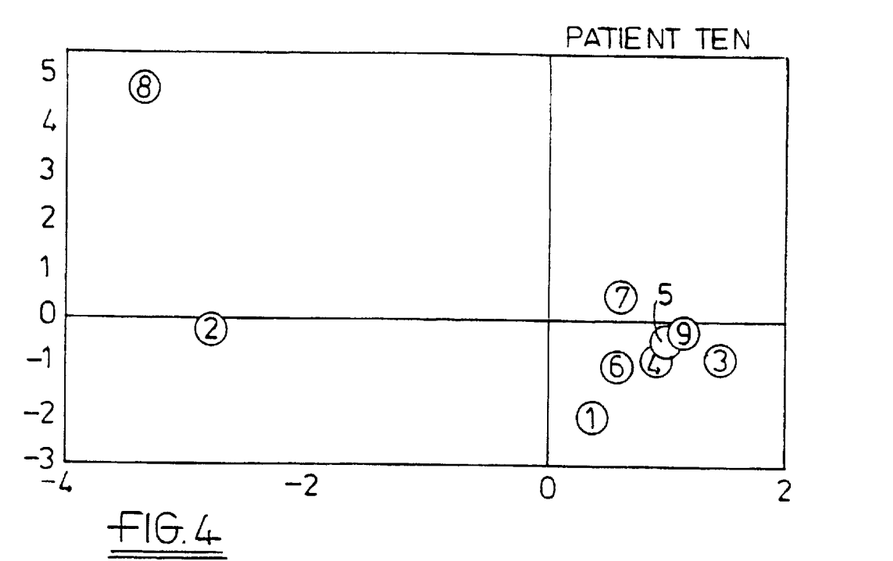
FIG. 4 shows response as a function of time for patient ten.

In thirteen out of fifteen patients in the study, the responses obtained with the A20S instrument correlated with the clinical healing progress of the patients. FIGS. 2 to 4 show illustrative results. In these Figures, responses are shown in the form of a Sammon map: each response, which comprises the outputs of the twenty individual sensors in the array, is reduced to two dimensions by the non-linear mapping technique of Sammon (see International Publication No. WO 95/33848 and references therein). The number within each circle is indicative of the week in which the measurement was taken. FIG. 2 (patient #1) and 3 (patient #3) clearly show a dramatic shift in the response with time. In FIG. 2 the shift occurs between weeks #6 and #7; in FIG. 3 the shift is observed between weeks #7 and #8. The shifts in response profile correlate with the healing process. FIG. 4, corresponding to patient #10, shows a large difference in response at week #8, followed by a reversion to the previous response type in week ten (week #2 appears to be an extraneous result). This correlates with a clinical relapse in ulcer healing suffered by patient #10.

The pathogenic organisms identified by the biopsies were found deep in the ulcer base. These organisms are often not detected by routine surface swabbing, but they are detectable by gas analysis with an array of gas sensors. Furthermore, and very importantly, the effectiveness of any treatment may be assessed by monitoring the gases and vapors produced by these organisms. Thus by compiling a database of response over the course of treatment, the effectiveness of any subsequent treatment may be monitored.

Since the response patterns are dependent on numerous factors, it is possible to correlate the observed responses with culturing conditions and derive more detailed information about the detected bacteria. Therefore, it may be possible to deduce the location of the bacterial infection from the response of the sensor array, or some other factor, such as pH.

EXAMPLE 2

Measurements were performed on the respiratory gases of two patients presenting with pulmonary candida albicans, using the AromaScan A32S instrument. Measurements of response patterns were made once a day over a period of five days.

Figure 6:
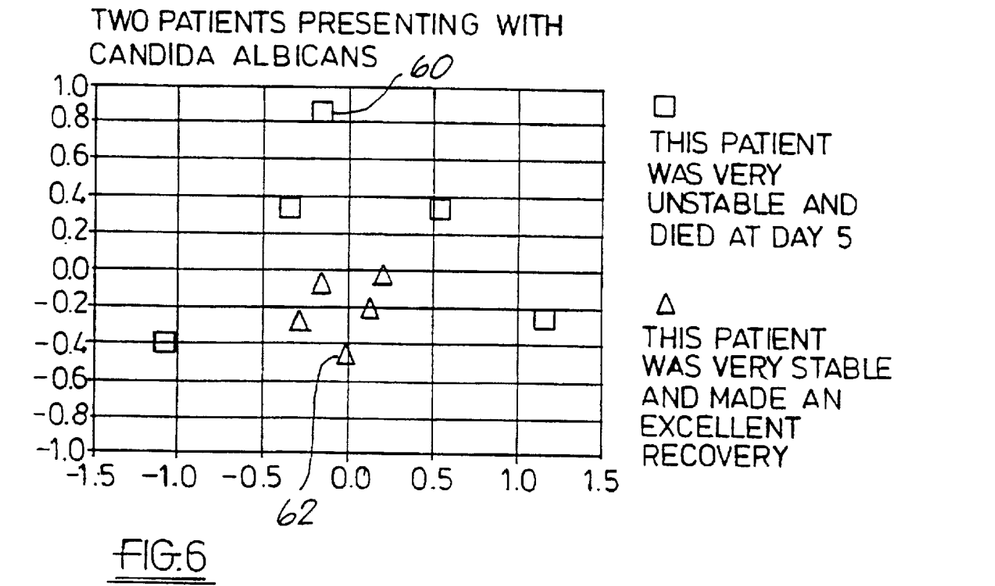
FIG. 6 shows response as a function of time for two patient s presenting with pulmonary candida albicans.

FIG. 6 shows the results in the form of a Sammon map, the rectangles 60 representing measurements of the respiratory gases of a first patient, and the triangles 62 representing measurements of the respiratory gases of a second patient. The data obtained from the second patient are quite stable, the response patterns being grouped in a tight cluster. This correlates with the fact that the patient was very stable, subsequently making an excellent recovery. In contrast, the response patterns obtained from the first patient vary greatly from day to day. This correlates with the fact that the patient was very unstable, and died on the fifth day of measurements.

Figure 1:
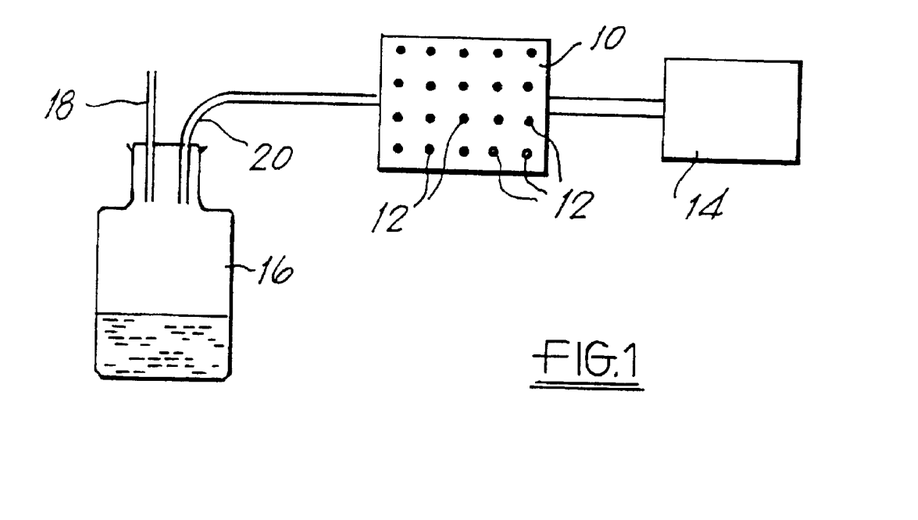
FIG. 1 depicts schematically apparatus for performing an improved method for identifying bacteria.

The invention comprises, in another aspect, a method for identifying a micro-organism comprising the steps of:

providing at least one gas sensor 12;

compiling a database 14 of responses to at least one known micro-organism under a variety of culturing conditions;

abstracting gas and/or vapor from a detection region 16 and flowing the same over the at least one gas sensor 12 and observing the response of the at least one sensor 12; and comparing the responses to the database 14.

As described above, International Publication No. WO 95/33848 discloses a method for identifying bacteria in which an array of gas sensors analyses gas or vapor produced by bacterial metabolism. The present invention recognizes that the method can be greatly improved by accounting for variations in culturing conditions. Such conditions include the nature of the nutrients (including the nature of any substrate involved in the culturing), the isolate employed, the incubation temperature and the stage in the bacterial life cycle at which measurements are made. It has been found that variation of these conditions can cause variations in metabolic profiles, and hence in the composition of the characteristic gases or vapors released by bacterial activity, thereby hampering or preventing the identification of the bacteria. In the present invention, variations in culturing conditions are accounted for by compiling a database of responses of the sensor array 10 to known bacteria under a variety of culturing conditions and relating the pattern obtained with an "unknown" sample to this database.

The present invention also recognizes that other microorganisms, such as viruses, fungi or parasites may be identified by detecting gases and/or vapors in this way.

The database preferably comprises responses to known micro-organisms under a variety of nutrient conditions, since such variations can greatly affect the composition of the gases or vapors emitted by the bacteria and detected in the present method. Thus, for example, the culturing media might comprise a modified broth, where one or more aminoacids are missing, or complex matrices, such as a blood based medium versus a peptone medium.

Preferably, the database further comprises responses to a plurality of different isolates of a single bacterial species.

The database may comprise responses to known bacteria incubated at a variety of temperatures, since the above described composition of gases or vapors is temperature dependent.

Additionally, the database may comprise responses to known bacteria obtained at different stages in the bacterial life cycle. The responses obtained from measurement of emitted gases or vapors vary as the bacteria pass through different metabolic phases, e.g. division (proliferation), growth arrest (product production/secretion), apoptosis or morbidity through starvation or external causation. Thus, it is possible to derive from the array response, in addition to the identity of bacteria, more detailed information concerning the condition of the bacteria and to avoid a negative result from a known bacterium presented in a condition not previously encountered, for which, however, the database needs to be comprehensive. Furthermore, by measuring a culture at a stage where only a few bacteria are present, and following the growth curve of the emitted gases and vapors, it is possible to discriminate between bacterial cultures at a very early stage of growth.

In the present embodiment, a sensor array 10 comprising a plurality of semiconducting polymer gas sensors is employed. It is quite possible that arrays of other types of gas sensors, such as MOS, SAW and quartz resonator devices, or combinations thereof, are also suitable for the present purposes. The semiconducting polymer array 10 is a commercially available, twenty or thirty two sensor instrument (A20S and A32S, manufactured by AromaScan plc, Crewe, UK). Gas detection is accomplished by measuring changes in de electrical resistance, these changes being caused by exposure of the sensors 12 to the gas. Thus, the response of the sensor array 10 is the pattern of resistance changes across the array 10. Usually, the response is normalised in an appropriate manner.

Pattern recognition is achieved with a neural network 14, which should be considered to be a "database" for the present purposes. The neural network 14 is trained to recognize the response pattern associated with known bacteria under a variety of culturing conditions. Thereafter, when an unknown response pattern is presented to the neural network 14, comparison with the response patterns used for training is made, via the outputs of the nodes embedded within the neural network architecture. More information concerning suitable neural networks may be found in International Publication No. WO 96/26492 and references therein.

It should be noted that other sensor interrogation techniques other than measurements of d.c. resistance are within the scope of the invention.

An important aspect of the present invention is the identification of at least one condition in a patient in which gas and/or vapor produced by the patient, or by a sample obtained from the patient, is flowed over the at least one gas sensor(s). Examples of such samples are respiratory gases or swabbed samples, such as described in Example 1 and 2. In this instance, where a separate culturing step is not performed, it is not possible to provide standardised growth conditions—the growth conditions experienced by the micro-organism in question are those provided in vivo. Preferably, at least a portion of the database is compiled from the responses of the sensor(s) to gas and/or vapor produced by a patient, or a sample obtained from the patient. In other words, response data such as that presented in Examples 1 and 2 can be used to compile the database. In this way, the database comprises responses to known microorganisms obtained at different stages during the course of treatment. Furthermore, the comparison of sensor response to the database can be used to indicate the severity or progression of an infection.

EXAMPLE 3

The importance of accounting for culturing conditions is illustrated by a study of six different species (*E. Coli, Staph*

*aureus*, Coagulase negative staphylococci, Group A Streptococcus and *Proteus mirabilis*) using the A32S instrument.

Ten different clinical isolates of the six bacterial species were collected and cultured. Each specimen was cultured on the appropriate medium and incubated at 37° C. for 24 hours.

Forty mls of sterile nutrient broth (Difco) in a sterile 250 ml Duran bottle were inoculated with each isolate and incubated at 37° C. for 24 hours. Thereafter a 1:10 dilution of the broth was made, again in a sterile Duran bottle and incubated for one hour.

The bottles were removed from incubation and the caps changed for caps having inlet 18 and outlet 20 ports (see FIG. 1). Each bottle was connected to the A32S sensor array 10 for sampling, thereby providing sixty response patterns. These response patterns were used to train the neural network to recognize the six abovementioned bacterial species.

The system was then tested with ten isolates of each of the six bacterial species (i.e. a total of sixty samples). The isolates employed were different to the isolates used for training the neural network, and were introduced to the system in a random order.

Of the sixty samples, fifty eight were recognized by the neural network (97% success rate). Two specimens were labelled "unknown". In all fifty eight cases of accurate recognition, the confidence of recognition lay in the range 89 to 100%.

TABLE 1

| Patient | Age/Sex | Biopsy Result | Time to observe response change (weeks) | Comments |
|---|---|---|---|---|
| 1 | 64/F | S. aureus | 6 | See FIG. 2. Improvement started at 3rd visit. Huge improvement at week 6. |
| 2 | 74/M | β-haemolytic strep | 4 | Marked improvement week 3. |
| 3 | 75/F | β-haemolytic strep-Proteus | 7 | See FIG. 3. Steady improvement weeks 4–10. |
| 4 | 67/M | β-haemolytic strep/Pseudomonas sp. | 5 | Huge improvement by week 5. |
| 5 | 71/F | No bacterial growth | 2 | Improvement week 3. |
| 6 | 74/M | β-haemolytic strep/S. aureus Proteus sp. | 6 | Remained healed. Slow improvement weeks 2–7. |
| 7 | 81/M | β-haemolytic strep/S. aureus | 4 | Improvement by week 4. |
| 8 | 60/M | β-haemolytic strep/S. aureus | 10 | Improvement weeks 6–14 |
| 9 | 71/F | β-haemolytic strep | 6 | Slow improvement weeks 4–8. |
| 10 | 80/M | β-haemolytic strep | 7 | See FIG. 4. Ulcer granulating weeks 3, followed by steady improvement until clinical relapse at week 9. |
| 11 | 79/F | No bacterial growth | 2 | Improvement weeks 3–5. |
| 12 | 55/F | β-haemolytic strep | 5 | Steady improvement weeks 2–7. |
| 13 | 69/M | β-haemolytic strep/Pseudomonas sp. | 5 | Rapid healing weeks 4–6. |
| 14 | 52/M | Peptostreptococcus sp. | 4 | Slow improvement weeks 3–9. |
| 15 | 81/F | β-haemoltyic strep/Proteus sp. | 2 | marked improvement week 2. |

What is claimed is:

1. A method for monitoring at least one condition in a patient comprising the steps of:

obtaining samples from the patient over a period of time;

flowing the samples, or gases associated with or produced by the samples, over at least one gas sensor;

measuring the response or responses of the at least one gas sensor; and correlating the response or responses with the occurrence or state of the at least one condition.

2. The method according to claim 1 in which the samples comprise respiratory gases.

3. The method according to claim 1 in which the samples comprise swabbed samples obtained from the patient.

4. The method according to claim 1 in which the samples comprise blood.

5. The method according to claim 1 in which the condition monitored is a disease state.

6. The method according to claim 5 in which the progression and/or the regression of the disease state is monitored.

7. The method according to claim 5 in which the condition is a bacterial infection.

8. The method according to claim 5 in which the condition is a viral, fungal or parasitic infection.

9. The method according to claim 1 in which the response or responses are correlated with the effectiveness of a course of treatment.

10. The method according to claim 1 in which the response or responses are correlated with progress of a healing process.

11. The method according to claim 1 in which the response or responses are correlated with the occurrence or state of the condition or conditions by a trained neural network.

12. The method according to claim 1 in which an array of gas sensors is employed.

13. The method according to claim 12 in which the pattern of responses of the sensors in the array is correlated with the occurrence of or state of the at least one condition.

14. The method according to claim 1 in which the samples are obtained continuously from the patient.

15. The method according to claim 14 in which the samples, or gas associated with or produced by the samples, are continuously flowed over the at least one gas sensor.

16. The method according to claim 15 in which the response or responses of the at least one gas sensor is measured continuously.

17. The method according to claim 14 in which a plurality of measurements are made over a period of time.

18. The method according to claim 14 in which the samples comprise respiratory gases obtained from a ventilator.

19. The method according to claim 14 in which the samples comprise blood undergoing a dialysis treatment.

20. The method according to claim 19 in which gases produced by a waste product containing solution are measured by the at least one gas sensor.

21. The method according to claim 20 in which the removal of urea from the blood sample is monitored by measuring ammonia evolved from the waste product containing solution.

22. The method for identifying a micro-organism comprising the steps of:

providing at least one gas sensor;

compiling a database of responses to at least one known micro-organism under a variety of culturing conditions;

abstracting gas or vapor from a detection region and flowing the same over said the at least one gas sensor and observing the response of the sensor or sensors; and comparing the response to the database.

23. The method according to claim 22 in which the database further comprises responses to at least one known bacterium.

24. The method according to claim 22 in which the database comprises responses to a plurality of different isolates of a single bacterial species.

25. The method according to claim 22 in which the micro-organism comprises a virus, fungus or parasite.

26. The method according to claim 22 in which the database comprises responses to at least one known micro-organism cultured under a variety of nutrient conditions.

27. The method according to claim 22 in which the database comprises responses to at least one known micro-organism cultured at a variety of temperatures.

28. The method according to claim 22 in which the database comprises responses to at least one known micro-organism obtained at different stages in the life cycle of the micro-organism.

29. The method for identifying at least one condition in a patient according to claim 22 in which gas and/or vapor produced by the patient, or by a sample obtained from the patient, is flowed over the at least one gas sensor.

30. The method according to claim 29 in which the at least a portion of the database is compiled from the responses of at least one gas sensor to gas and/or vapor produced by a patient, or by a sample obtained from the patient.

31. The method according to claim 22 in which the database comprises responses to at least one known micro-organism obtained at different stages during the course of treatment.

32. The method according to claim 22 in which an array of gas sensors is employed.

33. The method according to claim 22 in which the compilation of the database comprises training a neural network.

34. The method according to claim 22 in which the response of the sensors is used to provide information about the detection region.

35. The method according to claim 22 in which the gas sensor or sensors comprise a gas sensitive material.

36. The method according to claim 35 in which an electrical property of the gas sensitive material varies on exposure to gases.

37. The method according to claim 36 in which the gas sensitive material comprises semiconducting polymer.

38. The method according to claim 35 in which the gas sensor or sensors comprise MOS, quartz resonator or SAW devices.

* * * * *